(12) United States Patent
Cheng et al.

(10) Patent No.: US 8,471,100 B2
(45) Date of Patent: Jun. 25, 2013

(54) ENVIRONMENTAL STRESS-INDUCIBLE PROMOTER AND ITS APPLICATION IN CROPS

(75) Inventors: (Max) Zong-Ming Cheng, Knoxville, TN (US); Xia Ye, Zhengzhou (CN)

(73) Assignee: University of Tennessee Research Foundation, Knoxville, TN (US)

( * ) Notice: Subject to any disclaimer, the term of this patent is extended or adjusted under 35 U.S.C. 154(b) by 427 days.

(21) Appl. No.: 12/770,943

(22) Filed: Apr. 30, 2010

(65) Prior Publication Data

US 2010/0293667 A1 Nov. 18, 2010

Related U.S. Application Data

(60) Provisional application No. 61/178,663, filed on May 15, 2009.

(51) Int. Cl.
*C07H 21/04* (2006.01)
*A01H 1/00* (2006.01)
*A01H 5/00* (2006.01)
*C12N 15/82* (2006.01)

(52) U.S. Cl.
USPC ....... 800/279; 536/24.1; 435/320.1; 800/298; 800/300; 800/278; 800/289

(58) Field of Classification Search
None
See application file for complete search history.

(56) References Cited

U.S. PATENT DOCUMENTS

| | | |
|---|---|---|
| 4,535,060 A | 8/1985 | Comai et al. |
| 4,769,061 A | 9/1988 | Comai |
| 4,940,835 A | 7/1990 | Shah et al. |
| 4,971,908 A | 11/1990 | Kishore et al. |
| 5,145,783 A | 9/1992 | Kishore et al. |
| 5,188,642 A | 2/1993 | Shah et al. |
| 5,310,667 A | 5/1994 | Eichholtz et al. |
| 5,312,910 A | 5/1994 | Kishore et al. |
| 5,316,931 A | 5/1994 | Donson et al. |
| 5,366,892 A | 11/1994 | Foncerrada et al. |
| 5,380,831 A | 1/1995 | Adang et al. |
| 5,436,391 A | 7/1995 | Fujimoto et al. |
| 5,463,175 A | 10/1995 | Barry et al. |
| 5,491,288 A | 2/1996 | Chaubet et al. |
| 5,510,471 A | 4/1996 | Lebrun et al. |
| 5,589,367 A | 12/1996 | Donson et al. |
| 5,602,321 A | 2/1997 | John |
| 5,627,061 A | 5/1997 | Barry et al. |
| 5,633,435 A | 5/1997 | Barry et al. |
| 5,633,448 A | 5/1997 | Lebrun et al. |
| 5,703,049 A | 12/1997 | Rao |
| 5,723,756 A | 3/1998 | Peferoen et al. |
| 5,737,514 A | 4/1998 | Stiffler |
| 5,747,450 A | 5/1998 | Ohba et al. |
| 5,776,760 A | 7/1998 | Barry et al. |
| 5,792,931 A | 8/1998 | Duvick et al. |
| 5,804,425 A | 9/1998 | Barry et al. |
| 5,850,016 A | 12/1998 | Jung et al. |
| 5,866,775 A | 2/1999 | Eichholtz et al. |
| 5,866,785 A | 2/1999 | Donson et al. |
| 5,885,801 A | 3/1999 | Rao |
| 5,885,802 A | 3/1999 | Rao |
| 5,889,190 A | 3/1999 | Donson et al. |
| 5,889,191 A | 3/1999 | Turpen |
| 5,990,389 A | 11/1999 | Rao et al. |
| RE36,449 E | 12/1999 | Lebrun et al. |
| 6,040,497 A | 3/2000 | Spencer et al. |
| 6,248,876 B1 | 6/2001 | Barry et al. |
| RE37,287 E | 7/2001 | Lebrun et al. |
| 2006/0080747 A1 * | 4/2006 | Keetman et al. ............. 800/278 |

FOREIGN PATENT DOCUMENTS

| | | |
|---|---|---|
| WO | WO 97/04103 A2 | 2/1997 |
| WO | WO 97/04114 A2 | 2/1997 |
| WO | WO 00/66746 A1 | 11/2000 |
| WO | WO 00/66747 A1 | 11/2000 |
| WO | WO 00/66748 A1 | 11/2000 |
| WO | WO 01/66704 A2 | 9/2001 |

OTHER PUBLICATIONS

Saha et al., In Silico Biol 7:(1)7-19 (2007).*
Huang et al. Mol Biol Rep 39:969-87 (2012).*
Chalfie, M. et al. "Green Fluorescent Protein as a Marker for Gene Expression," *Science*, 1994, pp. 802-805, vol. 263, No. 5148.
Chiu, W. et al. "Engineered GFP as a vital reporter in plants," *Current Biology*, 1996, pp. 325-330, vol. 6, No. 3.
De Block, M. et al. "Engineering herbicide resistance in plants by expression of a detoxifying enzyme," *The European Molecular Biology Organization Journal*, 1987, pp. 2513-2518, vol. 6, No. 9.
De Wet, J. R. et al. "Firefly Luciferase Gene: Structure and Expression in Mammalian Cells," *Molecular and Cellular Biology*, 1987, pp. 725-737, vol. 7, No. 2.
Geiser, M. et al. "The hypervariable region in the genes coding for entomopathogenic crystal proteins for *Bacillus thuringiensis*: nucleotide sequence of the kurhd1 gene of subsp. kurstaki HD1," *Gene*, 1986, pp. 109-118, vol. 48.
Goff, S. A. et al. "Transactivation of anthocyanin biosynthetic genes following transfer of *B* regulatory genes into maize tissues." *The European Molecular Biology Organization Journal*, 1990, pp. 2517-2522, vol. 9, No. 8.

(Continued)

*Primary Examiner* — David H Kruse
*Assistant Examiner* — Russell Boggs
(74) *Attorney, Agent, or Firm* — Saliwanchik, Lloyd & Eisenschenk (57) ABSTRACT

The subject application provides polynucleotides, compositions thereof and methods for regulating gene expression in a plant using a promoter that initiates transcription in an inducible manner. In a further aspect of the invention, methods for modulating expression of a gene product in a stably transformed plant comprising the steps of (a) transforming a plant cell with a DNA construct comprising the disclosed promoter or fragments thereof that are capable of driving the expression of an operably linked nucleic acid sequence operably linked to at least one nucleotide sequence; (b) growing the plant cell under plant growing conditions and (c) regenerating a stably transformed plant from the plant cell wherein the induced expression of the operably linked nucleotide sequence alters the phenotype of the plant.

19 Claims, 1 Drawing Sheet
(1 of 1 Drawing Sheet(s) Filed in Color)

OTHER PUBLICATIONS

Gutha, L. R. & Reddy, A. R. "Rice *DREB1B* promoter shows distinct stress-specific responses, and the overexpression of cDNA in tobacco confers improved abiotic and biotic stress tolerance," *Plant Molecular Biology*, 2008, pp. 533-555, vol. 68.

Herrera-Estrella, L. et al. "Chimeric genes as dominant selectable markers in plant cells," *The European Molecular Biology Organization Journal*, 1983, pp. 987-995, vol. 2, No. 6.

Herrera-Estrella, L. et al. "Expression of chimaeric genes transferred into plant cells using a Ti-plasmid-derived vector," *Nature*, 1983, pp. 209-213, vol. 303.

Jones, D. A. et al. "Isolation of the tomato Cf-9 gene for resistance to *Cladosporium fulvum* by transposon tagging," *Science*, 1994, pp. 789-793, vol. 266, No. 5186.

Kim, K.-Y. et al. "A novel oxidative stress-inducible peroxidase promoter from sweetpotato: molecular cloning and characterization in transgenic tobacco plants and cultured cells," *Plant Molecular Biology*, 2003, pp. 831-838, vol. 51.

Ludwig, S. R. et al. "A Regulatory Gene as a Novel Visible Marker for Maize Transofrmation," *Science*, 1990, pp. 449-450, vol. 247, No. 4941.

Luehrsen, K. R. et al. "Transient Expression Analysis in Plants Using Firefly Luciferase Reporter Gene," *Methods in Enzymology*, 1992, pp. 397-414, vol. 216.

Martin, G. W. et al. "Map-Based Cloning of a Protein Kinase Gene Conferring Disease Resistance in Tomato," *Science*, 1993, pp. 1432-1436, vol. 262, No. 5138.

Mindrinos, M. et al. "The *A. thaliana* Disease Resistance Gene RPS2 Encodes a Protein Containing a Nucleotide-Binding Site and Leucine-Rich Repeats," *Cell*, 1994, pp. 1089-1099, vol. 78.

Murray, E. E. et al. "Codon usage in plant genes," *Nucleic Acids Research*, 1989, pp. 477-498, vol. 17, No. 2.

Rai, M. et al. "Comparative functional analysis of three abiotic stress-inducible promoters in transgenic rice," *Transgenic Research*, 2009, pp. 787-799, vol. 18.

Riggs, C. D. & Chrispeels, M. J. "Luciferase reporter gene cassettes for plant gene expression studies," *Nucleic Acids Research*, 1987, pp. 8115, vol. 15, No. 19.

Schubert, P. et al. "Cloning of the Alcaligenes eutrophus Genes for Synthesis of Poly-β-Hydroxybutyric Acid (PHB) and Synthesis of PHB in *Escherichia coli*," *Journal of Bacteriology*, 1988, pp. 5837-5847, vol. 170, No. 12.

Yamaguchi-Shinozaki, K. & Shinozaki, K. "Organization of cis-acting regulatory elements in osmotic- and cold-stress-responsive promoters," *TRENDS in Plant Science*, 2005, pp. 88-94, vol. 10, No. 2.

Stalker, D. M. et al. "Herbicide Resistance in Transgenic Plants Expressing a Bacterial Detoxification Gene," *Science*, 1988, pp. 419-423, vol. 242, No. 4877.

Tran, L.-S. P. et al. "Isolation and Functional Analysis of Arabidopsis Stress-Inducible NAC Transcription Factors That Bind to a Drought-Responsive cis-Element in the early responsive to dehydration stress 1 Promoter," *The Plant Cell*, 2004, pp. 2481-2498, vol. 16.

Williamson, M. S. et al. "Nucleotide sequence of barley chymotrypsin inhibitor-2 (CI-2) and its expression in normal and high-lysine barley," *European Journal of Biochemistry*, 1987, pp. 99-106, vol. 165.

Li, Z. & Murai, N. "Agronomic trait evaluation of field-grown transgenic rice plants containing the hygromycin resistance gene and the maize Activator element," *Plant Science*, 1995, pp. 219-227, vol. 108.

Neeraja, C. N. et al. "A marker-assisted backcross approach for developing submergence-tolerant rice cultivars" *Theor Appl Genet*, 2007, pp. 767-776, vol. 115.

Ismail, A. M. et al. "Mechanisms associated with tolerance to flooding during germination and early seedling growth in rice" *Annals of Botany*, 2009, pp. 197-209, vol. 103.

Septiningsih, E. M. et al. "Identifying novel QTLs for submergence tolerance in rice cultivars IR72 and Madabaru" *Theor Appl Genet*, 2012, pp. 867-874, vol. 124.

Septiningsih, E. M. et al. "Development of submergence-tolerant rice cultivars: the *Sub1* locus and beyond" *Annals of Botany*, 2009, pp. 151-160, vol. 103.

Singh, N. et al. "Molecular marker survey and expression analyses of the rice submergence-tolerance gene *SUB1A*" *Theor Appl Genet*, 2010, pp. 1441-1453, vol. 121.

Thomashow, M. F. "Role of Cold-Responsive Genes in Plant Freezing Tolerance" *Plant Physiol.*, 1998, pp. 1-7, vol. 118.

Wahid, A. et al. "Heat tolerance in plants: An overview" *Environmental and Experimental Botany*, 2007, pp. 199-223, vol. 61.

Xu, K. et al. "*Sub1A* is an ethylene-response-factor-like gene that confers submergence tolerance to rice" *Nature*, Aug. 10, 2006, pp. 705-708, vol. 442.

Yamaguchi, T. et al. "Developing salt-tolerant crop plants: challenges and opportunities" *TRENDS in Plant Science*, Dec. 2005, pp. 615-620, vol. 10, No. 12.

Zhu, J.-K. "Plant salt tolerance" *TRENDS in Plant Science*, Feb. 2001, pp. 66-71, vol. 6, No. 2.

\* cited by examiner

SEQUENCE LISTING

<160> NUMBER OF SEQ ID NOS: 1

<210> SEQ ID NO 1
<211> LENGTH: 1508
<212> TYPE: DNA

-continued

```
<213> ORGANISM: poplar trees

<400> SEQUENCE: 1
aacaaccaca caatgtttta cctcacagat tgatcatagc tgtctttcct cttgatgtct      60
agctagatga tcaaatgcca tcttttaatt ttactacaag caagggaaca cataatgaga     120
catatattga actgcaaatt aacttttgct gtagggtttt agattctgtt tcattaaaaa     180
agcttatcat gtgtgtgtgt gtgtggtagc tcgtgacctt agaaatcagg atagattaga     240
agaaatttag gacaagatat gcacgcatca aggatacttg gatcaagata cagagggtcc     300
atttagaatc agataaaaag gttcataaat acaagaagag agagaccata tcctttcttt     360
ttgatgttga aggcaaactc tttatttatt tatttatctt ttacatagta aaaaaataat     420
aattttaata gttgcttccc aatattttgg attctagcct tcctcattaa tttctaagct     480
tttttttttt tttaaaaaa aagaaaagta gcaaagggta atttcagctg gttactgtac     540
atcaaaacta aattattgtt taataaaatc ttaagcaaaa ccattcatat atagcagcac     600
ttataaaaaa gaatatttct tgcaacctgc agcccaatc ttcaatattt acatcctttc     660
caaatttatt tttcaaagaa ttaatttcaa ctcattaacg tcaatgcacg agattcttat     720
atatgatctc gagaaagata ttcggttaac attactctct tttttatacc tatccttctc     780
atgcgtgcgt gaagcataat tatgatcaac acaatcatta ttaatatagt tatcctgaac     840
ttggtatata ttaaatttta aatctattag catgtccaag agatcaggag cagacttcca     900
aacaatattc aataagattt ttttctcctc ggacaatcta ttaagaaaat tctttcctct     960
tggccaacca tttccactat atatcacaga tattttaaga ataaatattt gtgtatatat    1020
ggtatgcatg aggaaaatat tttttttata ttattacgca gtagataaag cccagctgga    1080
tgatcaattc tttatgagaa ttaaaatatt tttgtgtgct gtatcctttt ttattactgg    1140
cacaacaaaa tcaaacgaca atatatatat atcaagggaa attaattatc tcaaatatgc    1200
aaaatttaaa tttggcaacg tttttctatt ttttttcagc aataatattg gaaaattgta    1260
ctttactcta agcatgtaat tattgtcgaa atcttcattt tggagggaaa gaaataaata    1320
tggtagtaac attaaatgtt ggaatatttt ttgagattcc tggagggaag gccaataagg    1380
ccctgttcca agtagtcttt aaaggctcca ctctttggta tttaccatct ctcttttcct    1440 tcttttcat cttcaacccc tagctaatta agaagaaaaa tgttgtttaa tatttcttgt    1500
ttacggtt                                                             1508
```

ENVIRONMENTAL STRESS-INDUCIBLE PROMOTER AND ITS APPLICATION IN CROPS

CROSS-REFERENCE TO RELATED APPLICATION

This application claims the benefit of U.S. Provisional Application Ser. No. 61/178,663, filed May 15, 2009, the disclosure of which is hereby incorporated by reference in its entirety, including all figures, tables and amino acid or nucleic acid sequences.

This invention was made with United States Government support under DOE Grant No. DE-AC05-00OR22725, Subcontract No. UT-4000063906. The United States Government has certain rights in the invention.

BACKGROUND OF THE INVENTION

Recent advances in plant genetic engineering have enabled the engineering of plants having improved characteristics or traits, such as disease resistance, insect resistance, herbicide resistance, enhanced stability or shelf-life of the ultimate consumer product obtained from the plants and improvement of the nutritional quality of the edible portions of the plant. Thus, one or more desired genes from a source different than the plant, but engineered to impart different or improved characteristics or qualities, can be incorporated into the plant's genome. One or more new genes can then be expressed in the plant cell to exhibit the desired phenotype such as a new trait or characteristic.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, drought, flooding, salt or toxins.

Environmental stresses cause billions of dollars of economic losses to crops and forest by yield and quality losses. Globally, the most commonly encountered environmental stresses are heat stress due to high temperature, freeze or chilly stress due to low temperature, drought due to water shortage and flooding due to excessive water. A limited number of genetically engineered crops and trees have been or under field tests for commercial release, for example, drought-tolerant maize by Monsanto and cold hardy Eucalyptus tree by ArborGen. Many currently used stress-tolerance genes are more specific to one stress, such as DHS for drought tolerance, and CBF2 for cold hardiness, and engineering these genes under constitutive promoter (universally expressing) can cause abnormal phenotypes because many of these genes are developmentally regulated. Therefore, it would be highly desirable to express these stress-tolerance genes only when stresses are upon to plants, and this can be done by use of tightly regulated, stress-inducible promoters.

SUMMARY OF THE INVENTION

The subject application provides polynucleotides, compositions thereof and methods for regulating gene expression in a plant. Polynucleotides disclosed herein comprise novel sequences for a promoter that initiates transcription in an inducible manner. Further embodiments of the invention comprise the nucleotide sequence of SEQ ID NO: 1 or fragments thereof that are capable of driving the expression of an operably linked nucleic acid sequence. Other polynucleotides disclosed herein provide nucleotide sequences having at least 70% sequence identity to the sequence set forth in SEQ ID NO: 1. Polynucleotides complementary to such polynucleotides (polynucleotide sequences having at least 70% sequence identity to SEQ ID NO: 1) are also provided by the subject application.

Additionally, DNA constructs (sometimes referred to as nucleotide constructs) comprising a promoter, as disclosed herein, operably linked to a heterologous nucleotide sequence of interest wherein said promoter is capable of driving expression of the operably linked heterologous nucleotide sequence in a plant cell are provided. Further aspects of the invention provide expression vectors and plants, seed or plant cells having stably incorporated into their genomes a DNA construct as disclosed herein.

Methods of selectively expressing a nucleotide sequence in a plant, comprising transforming a plant cell with a DNA construct, as disclosed herein, and optionally regenerating a transformed plant from said plant cell are also provided. The DNA construct comprises a promoter and a heterologous nucleotide sequence operably linked to said promoter, wherein said promoter initiates transcription of said nucleotide sequence in a plant cell in an inducible manner. Thus, the promoter disclosed herein is useful for controlling the expression of operably linked coding sequences in an inducible manner.

Downstream from and under the transcriptional initiation regulation of the promoter will be a sequence of interest that will provide for modification of the phenotype of the plant. Such modification caused by the sequence of interest includes modulating the production of an endogenous product, as to amount or relative distribution or the production of an exogenous expression product to provide for a novel function or product in the plant. For example, a heterologous nucleotide sequence that encodes a gene product that confers pathogen, herbicide, salt, cold, drought, or insect resistance.

In a further aspect of the invention, methods for modulating expression of a gene product in a stably transformed plant comprising the steps of (a) transforming a plant cell with a DNA construct comprising the disclosed promoter or fragments thereof that are capable of driving the expression of an operably linked nucleic acid sequence operably linked to at least one nucleotide sequence; (b) growing the plant cell under plant growing conditions and (c) regenerating a stably transformed plant from the plant cell wherein the induced expression of the operably linked nucleotide sequence alters the phenotype of the plant.

BRIEF DESCRIPTION OF THE DRAWING

The patent or application file contains at least one drawing executed in color. Copies of this patent or patent application publication, with color drawing, will be provided by the Office upon request and payment of the necessary fee.

DETAILED DESCRIPTION OF THE INVENTION

The subject invention also provides isolated, recombinant, and/or purified polynucleotide sequences comprising:

a) a polynucleotide sequence comprising SEQ ID NO: 1 or fragments thereof that are capable of driving the expression of an operably linked nucleic acid sequence;

b) a polynucleotide sequence having at least about 70% to 99.99% identity to a polynucleotide sequence comprising SEQ ID NO: 1 or fragments thereof that are capable of driving the expression of an operably linked nucleic acid sequence;

c) a polynucleotide that is fully complementary to the polynucleotides set forth in (a) or (b);

d) a DNA construct comprising a polynucleotide sequence as set forth in (a), (b) or (c) operably linked to a heterologous nucleotide (polynucleotide) sequence;

e) a host cell comprising a vector as set forth in (d);

f) a polynucleotide that hybridizes under low, intermediate or high stringency with a polynucleotide sequence as set forth in (a), (b) or (c); or g) a probe comprising a polynucleotide according to (a), (b) or (c) and, optionally, a label or marker.

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

A homologous polynucleotide or polypeptide sequence, for the purposes of the present invention, encompasses a sequence having a percentage identity with the polynucleotide or polypeptide sequences, set forth herein, of between at least (or at least about) 20.00% to 99.99% (inclusive). The aforementioned range of percent identity is to be taken as including, and providing written description and support for, any fractional percentage, in intervals of 0.01%, between 20.00% and, up to, including 99.99%. These percentages are purely statistical and differences between two nucleic acid sequences can be distributed randomly and over the entire sequence length. For example, homologous sequences can exhibit a percent identity of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the full length, native, and/or naturally occurring polynucleotide. The terms "identical" or percent "identity", in the context of two or more polynucleotide or polypeptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection. In certain aspects of the invention, homologous sequences to SEQ ID NO: 1 have at least 70% sequence identity to SEQ ID NO: 1 over its full length (or over the full length of a given fragment of SEQ ID NO: 1).

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3): 403-410; Thompson et al., 1994, *Nucleic Acids Res.* 22(2): 4673-4680; Higgins et al., 1996, *Methods Enzymol.* 266:383-402; Altschul et al., 1990, *J. Viol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence". In various aspects of the invention, sequences are "fully complementary" to a reference sequence (e.g., SEQ ID NO: 1). The phrase "fully complementary" refers to sequences contain no mismatches in their base pairing.

Sequence homology and sequence identity can also be determined by hybridization studies under high stringency, intermediate stringency, and/or low stringency. Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak [1987] *DNA Probes*, Stockton Press, New York, N.Y., pp. 169-170.

For example, hybridization of immobilized DNA on Southern blots with $^{32}$P-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5×Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$$Tm = 81.5°\ C. + 16.6\ \text{Log}\ [Na^+] + 0.41(\%\ G+C) - 0.61(\%\ \text{formamide}) - 600/\text{length of duplex in base pairs.}$$

Washes are typically carried out as follows:

(1) twice at room temperature for 15 minutes in 1×SSPE, 0.1% SDS (low stringency wash);

(2) once at $T_m$-20° C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$T_m(°\ C.)=2$(number T/A base pairs)$+4$(number G/C base pairs) (Suggs et al. [1981] *ICN-UCLA Symp. Dev. Biol. Using Purified Genes*, D. D. Brown [ed.], Academic Press, New York, 23:683-693).

Washes can be carried out as follows:

(1) twice at room temperature for 15 minutes 1×SSPE, 0.1% SDS (low stringency wash);

2) once at the hybridization temperature for 15 minutes in 1×SSPE, 0.1% SDS (intermediate stringency wash).

In general, salt and/or temperature can be altered to change stringency. With a labeled DNA fragment>70 or so bases in length, the following conditions can be used:

Low: 1 or 2×SSPE, room temperature
Low: 1 or 2×SSPE, 42° C.
Intermediate: 0.2× or 1×SSPE, 65° C.
High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5–20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006-13512.

The present invention further comprises fragments of the polynucleotide sequences of the instant invention. Representative fragments of the polynucleotide sequences according to the invention will be understood to mean any nucleotide fragment having at least 5 successive nucleotides, preferably at least 12 successive nucleotides, and still more preferably at least 15, 18, or at least 20 successive nucleotides of the sequence from which it is derived. The upper limit for such fragments is the total number of nucleotides found in the full-length sequence of SEQ ID NO: 1. The term "successive" can be interchanged with the term "consecutive" or the phrase "contiguous span". Thus, in some embodiments, a polynucleotide fragment may be referred to as "a contiguous span of at least X nucleotides, wherein X is any integer value between 5 and 1507 (one nucleotide less than the total number of nucleotides found in the full-length sequence (SEQ ID NO: 1))."

In some embodiments, the subject invention includes those fragments capable of hybridizing under various conditions of stringency conditions (e.g., high or intermediate or low stringency) with a nucleotide sequence according to the invention; fragments that hybridize with a nucleotide sequence of the subject invention can be, optionally, labeled as set forth below.

Thus, the subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides of SEQ ID NO: 1. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}$P, $^{35}$S, $^3$H, $^{125}$I) or with a molecule such as biotin, acetylaminofluorene, digoxigenin, 5-bromo-deoxyuridine, or fluorescein to provide probes that can be used in numerous applications.

The promoter sequences disclosed herein are useful for expressing operably linked nucleotide sequences in an inducible manner. As disclosed herein, SEQ ID NO: 1 is a promoter that is induced by several environmental stressors. These include heat (e.g., temperatures in excess of 40° C.), cold (e.g., temperatures of 4° C. or lower), drought (e.g., a set of environmental conditions under which a plant will begin to suffer the effects of water deprivation, such as decreased stomatal conductance and photosynthesis, decreased growth rate, loss of turgor (wilting), or ovule abortion. Water deprivation may be caused by lack of rainfall or limited irrigation. Alternatively, water deficit may also be caused by high temperatures, low humidity, saline soils, freezing temperatures or water-logged soils that damage roots and limit water uptake to the shoot) and flooding (refers to any stress which is associated with or induced by prolonged or transient immersion of a plant, plant part, tissue or isolated cell in a liquid medium such as occurs during monsoon, wet season, flash flooding or excessive irrigation of plants, etc.). As used an "isolated" or "purified" nucleic acid molecule, or biologically active fragment thereof, is substantially free of other cellular material or culture medium when produced by recombinant techniques, or substantially free of chemical precursors or other chemicals when chemically synthesized. An "isolated" nucleic acid is essentially free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The nucleic acid of SEQ ID NO: 1 is a promoter. The term "promoter" is intended to mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. The promoter elements that enable inducible expression, can be identified, isolated, and used with core promoters to confer a preferred expression pattern. In this aspect of the invention, a "core promoter" is intended to mean a promoter without promoter elements generally found upstream and/or downstream of the core promoter (the minimal portion of the promoter required to properly initiate transcription which includes a Transcription Start Site (TSS) a binding site for RNA polymerase and general transcription factor binding sites.

The term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this application) that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both. In the context of this disclosure, a post-transcriptional regulatory element may include elements that are active following transcription initiation, for example translational and transcriptional enhancers, translational and transcriptional repressors, and mRNA stability determinants.

The regulatory elements, or fragments thereof, may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events.

The promoter sequences disclosed herein, when assembled within a DNA construct such that the promoter is operably linked to a nucleotide sequence of interest, enable expression of the nucleotide sequence in the cells of a plant stably transformed with this DNA construct. The term "operably linked" is intended to mean that the transcription or translation of the heterologous nucleotide sequence is under the influence of the promoter sequence. "Operably linked" is also intended to mean the joining of two nucleotide sequences such that the coding sequence of each DNA fragment remain in the proper reading frame. In this manner, the nucleotide sequences for the promoters are provided in DNA constructs along with the nucleotide sequence of interest, typically a heterologous nucleotide sequence, for expression in the plant of interest. The term "heterologous nucleotide sequence" is intended to mean a sequence that is not naturally operably linked with the promoter sequence. While this nucleotide sequence is heterologous to the promoter sequence, it may be homologous, or native; or heterologous, or foreign, to the plant host. It is recognized that the promoters may be used with their native coding sequences to increase or decrease expression, thereby resulting in a change in phenotype of the transformed plant under certain conditions (e.g., heat, cold, drought or flooding).

Fragments and variants of the disclosed promoter sequences are also encompassed. A "fragment" is intended to mean a portion of the promoter sequence. Fragments of a promoter sequence may retain biological activity (the ability to drive expression of an operably linked nucleotide sequence in an inducible manner). Thus, for example, less than the entire promoter sequence disclosed herein may be utilized to drive expression of an operably linked nucleotide sequence of interest, such as a nucleotide sequence encoding a heterologous protein.

Accordingly, a fragment of the promoter of SEQ ID NO: 1 can contain a biologically active portion of the promoter or it may be a fragment that can be used as a hybridization probe or PCR primer using methods disclosed below. A biologically active portion of the promoter of SEQ ID NO: 1 can be prepared by isolating fragments of SEQ ID NO: 1 and assessing the activity of that fragment in causing the expression of an operably linked nucleic acid sequence (such as a reporter gene). Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 750, 800, 850, 900, 950, 1000, 1050, 1100, 1150, 1200, 1250, 1300, 1350, 1400, 1450, 1500 or up to one nucleotide fewer (i.e., 1507 nucleotides) than the number of nucleotides present in the full-length promoter nucleotide sequence disclosed herein, e.g., 1508 nucleotides for SEQ ID NO:1. Such fragments will usually comprise the TATA recognition sequence of the particular promoter sequence and can be obtained by use of restriction enzymes to cleave the naturally occurring promoter nucleotide sequence disclosed herein; by synthesizing a nucleotide sequence from the naturally occurring sequence of the promoter DNA sequence; or through the use of PCR technology. See particularly, Mullis et al. (1987) *Methods Enzymol.* 155:335-350, and Erlich, ed. (1989) *PCR Technology* (Stockton Press, New York). Variants of these promoter fragments, such as those resulting from site-directed mutagenesis and a procedure such as DNA "shuffling", are also encompassed by the instant disclosure.

The term "variants" is intended to mean sequences having substantial similarity with a promoter sequence disclosed herein. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence will have at least 40%, 50%, 60%, 65%, 70%, generally at least 75%, 80%, 85%, 90%, 91%, 92%, 93%, 94%, to 95%, 96%, 97%, 98%, 99% or more sequence identity to that particular nucleotide sequence (e.g., SEQ ID NO: 1) as determined by sequence alignment programs described elsewhere herein using default parameters. Biologically active variants are also encompassed. Biologically active variants include, for example, the native promoter sequence having one or more nucleotide substitutions, deletions, or insertions. Promoter activity may be measured by using techniques such as Northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Cold Spring Harbor, N.Y.), hereinafter "Sambrook," herein incorporated by reference. Alternatively, levels of a reporter gene such as green fluorescent protein (GFP) or the like produced under the control of a promoter fragment or variant can be measured. See, for example, U.S. Pat. No. 6,072,050, herein incorporated by reference. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein.

Variant promoter nucleotide sequences also encompass sequences derived from a mutagenic and recombinogenic procedure such as DNA shuffling. With such a procedure, one or more different promoter sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad Sci. USA* 94:4504-4509; Crameri et al. (1998) *Nature* 391:288-291; and U.S. Pat. Nos. 5,605,793 and 5,837,458.

The nucleotide sequences disclosed herein can be used to isolate corresponding sequences from other organisms, particularly other plants, for example, other monocots. In this manner, methods such as PCR, hybridization, and the like can be used to identify such sequences based on their sequence homology to the sequence set forth herein. Sequences isolated on the basis of sequence identity to SEQ ID NO: 1, or to fragments thereof, are encompassed by this disclosure. Corresponding sequences may be isolated from any plant, including, but not limited to corn (*Zea mays*), *Brassica* (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus carica*), guava (*Psidium guajava*), mango (*Mangifera indica*), olive (*Olea europaea*), oats, barley, vegetables, ornamentals, and conifers. Plants include corn, soybean, sunflower, safflower, *Brassica* or canola, wheat, barley, rye, alfalfa, and sorghum.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, supra. See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

The promoter sequence disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct, including a nucleic acid DNA construct that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA.

As used herein, the term "plant" includes reference to whole plants, plant organs (e.g., leaves, stems, roots, etc.), seeds, plant cells, and progeny of same. Parts of transgenic plants are to be understood within the scope of the invention comprise, for example, plant cells, protoplasts, tissues, callus, embryos as well as flowers, stems, fruits, ovules, leaves, or roots originating in transgenic plants or their progeny previously transformed with a DNA molecule of the invention, and therefore consisting at least in part of transgenic cells. As used herein, the term "plant cell" includes, without limitation, seeds suspension cultures, embryos, meristematic regions, callus tissue, leaves, roots, shoots, gametophytes, sporophytes, pollen, and microspores. Monocotyledonous and dicotyledonous plants can be transformed with a promoter or DNA construct as disclosed herein.

The promoter sequences and methods disclosed herein are useful in regulating expression of any heterologous nucleotide sequence in a host plant. Thus, the heterologous nucleotide sequence operably linked to the promoters disclosed herein may be a structural gene encoding a protein of interest. Genes of interest are reflective of the commercial markets and interests of those involved in the development of the crop. General categories of genes of interest include, for example, those genes involved in information, such as zinc fingers, those involved in communication, such as kinases, and those involved in housekeeping, such as heat shock proteins. More specific categories of transgenes, for example, include genes encoding proteins conferring resistance to abiotic stress, such as drought, flooding, temperature (heat or cold), salinity, and toxins such as pesticides and herbicides, or to biotic stress, such as attacks by fungi, viruses, bacteria, insects, and nematodes, and development of diseases associated with these organisms. Various changes in phenotype are of interest including modifying expression of a gene in a specific plant tissue, altering a plant's pathogen or insect defense mechanism, increasing the plant's tolerance to herbicides, altering tissue development to respond to environmental stress, and the like. The results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrients uptake in the plant. These changes result in a change in phenotype of the transformed plant.

It is recognized that any gene of interest can be operably linked to the promoter sequences disclosed herein and expressed in plant tissues. Thus, a DNA construct comprising a gene of interest, such as those described below, to create plants having a desired phenotype (e.g., disease, herbicide or insect resistance), to create heat or cold tolerance in a plant or to create or enhance resistance to drought or flood conditions in a plant. Accordingly, this disclosure encompasses methods that are directed to protecting plants against flooding, drought, heat, cold, fungal pathogens, bacteria, viruses, nematodes, insects, and the like. By "disease resistance" or "insect resistance" is intended that the plants avoid the harmful symptoms that are the outcome of the plant-pathogen interactions.

Disease resistance and insect resistance genes such as lysozymes, cecropins, maganins, or thionins for antibacterial protection, or the pathogenesis-related (PR) proteins such as glucanases and chitinases for anti-fungal protection, or *Bacillus thuringiensis* endotoxins, protease inhibitors, collagenases, lectins, and glycosidases for controlling nematodes or insects are all examples of useful gene products. Pathogens include, but are not limited to, viruses or viroids, bacteria, insects, nematodes, fungi, and the like. Viruses include tobacco or cucumber mosaic virus, ringspot virus, necrosis virus, maize dwarf mosaic virus, etc. Nematodes include parasitic nematodes such as root knot, cyst, and lesion nematodes, etc.

Genes encoding disease resistance traits include detoxification genes, such as against fumonisin (U.S. Pat. No. 5,792,931) avirulence (avr) and disease resistance (R) genes (Jones et al. (1994) *Science* 266:789; Martin et al. (1993) *Science* 262:1432; Mindrinos et al. (1994) *Cell* 78:1089); and the like. Insect resistance genes may encode resistance to pests that have great yield drag such as rootworm, cutworm, European corn borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or Basta® (glufosinate) (e.g., the bar gene), or other such genes known in the art. The bar gene encodes resistance to the herbicide Basta®, the nptII gene encodes resistance to the antibiotics kanamycin and geneticin, and the ALS gene encodes resistance to the herbicide chlorsulfuron. Glyphosate resistance is imparted by mutant 5-enolpyruvl-3-phosphikimate synthase (EPSP) and aroA genes. See, for example, U.S. Pat. No. 4,940,835, which discloses the nucleotide sequence of a form of EPSPS which can confer glyphosate resistance. U.S. Pat. No. 5,627,061 also describes genes encoding EPSPS enzymes. See also U.S. Pat. Nos. 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over-expression of genes encoding glyphosate N-acetyltransferase.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-ketothiolase, PHBase (polyhydroxybutyrate synthase), and acetoacetyl-CoA reductase (see Schubert et al. (1988) *J. Bacteria* 170:5837-5847) facilitate expression of polyhydroxyalkanoates (PHAs).

Agronomically important traits that affect quality of grain, such as levels and types of oils, saturated and unsaturated, quality and quantity of essential amino acids, levels of cellulose, starch, and protein content can be genetically altered. Modifications include increasing content of oleic acid, saturated and unsaturated oils, increasing levels of lysine and sulfur, providing essential amino acids, and modifying starch. Hordothionin protein modifications in corn are described in U.S. Pat. Nos. 5,990,389; 5,885,801; 5,885,802 and 5,703,049; herein incorporated by reference. Another example is lysine and/or sulfur rich seed protein encoded by the soybean 2S albumin described in U.S. Pat. No. 5,850,016, and the chymotrypsin inhibitor from barley, Williamson et al. (1987)

*Eur. J. Biochem.* 165:99-106, the disclosures of which are herein incorporated by reference.

Exogenous products include plant enzymes and products as well as those from other sources including prokaryotes and other eukaryotes. Such products include enzymes, cofactors, hormones, and the like. Examples of other applicable genes and their associated phenotype include genes that confer viral resistance; genes that confer fungal resistance; genes that confer insect resistance; genes that promote yield improvement; and genes that provide for resistance to stress, such as dehydration resulting from heat and salinity, toxic metal or trace elements, or the like.

In one embodiment, DNA constructs will comprise a transcriptional initiation region comprising a promoter sequence, as disclosed herein, or variants or fragments thereof, operably linked to a heterologous nucleotide sequence whose expression is to be controlled by the promoter. Such a DNA construct is provided with a plurality of restriction sites for insertion of the nucleotide sequence to be under the transcriptional regulation of the regulatory regions. The DNA construct may additionally contain selectable marker genes.

Where appropriate, the heterologous nucleotide sequence whose expression is to be under the control of the promoter sequence disclosed herein may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477-498, herein incorporated by reference.

Reporter genes or selectable marker genes may be included in the DNA constructs. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330. Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481); phosphinothricin (DeBlock et al. (1987) *EMBO J.* 6:2513-2518). Other genes that could serve utility in the recovery of transgenic events but might not be required in the final product would include, but are not limited to, examples such as GUS (b-glucuronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.* 15(19): 8115 and Luehrsen et al. (1992) *Methods Enzymol.* 216:397-414), and the maize genes encoding for anthocyanin production (Ludwig et al. (1990) *Science* 247:449).

The nucleic acid molecules disclosed herein are useful in methods of expressing a nucleotide sequence in a plant. This may be accomplished by transforming a plant cell of interest with a DNA construct comprising a promoter identified herein, operably linked to a heterologous nucleotide sequence, and regenerating a stably transformed plant from said plant cell. The plant can then be exposed to environmental conditions (e.g., flooding, drought, heat or cold) that cause the promoter to drive expression of the heterologous nucleotide sequence.

Plant species suitable for transformation include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annum*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus carica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Other plants suitable for transformation with a promoter as disclosed herein include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Additionally, monocots, such as maize, rice, barley, oats, wheat, sorghum, rye, sugarcane, pineapple, yams, onion, banana, coconut, and dates.

As used herein, "vector" refers to a DNA molecule such as a plasmid, cosmid, or bacterial phage for introducing a nucleotide construct, for example, a DNA construct, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

Various methods disclosed herein include introducing a nucleotide (DNA) construct into a plant, The term "introducing" is used herein to mean presenting to the plant the nucleotide construct in such a manner that the construct gains access to the interior of a cell of the plant. These methods do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant. The nucleotide constructs disclosed herein may be introduced into plants by contacting plants with a virus or viral nucleic acids. Generally, such methods involve incorporating a nucleotide construct within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367, and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, Agrobacterium-mediated transformation (U.S. Pat. Nos. 5,981,840 and 5,563,055), direct gene transfer (Paszkowski et al. (1984) *EMBO J.* 3:2717-2722), and ballistic particle acceleration (see, for example, U.S. Pat. Nos. 4,945,050; 5,879,918; 5,886,244; 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants according to methods known in the art. See, for example, McCormick et al. (1986) *Plant Cell Reports* 5:81-84. These plants may then be grown, and either pollinated with the same transformed plant variety or different varieties, and the resulting hybrid having a desired phenotypic characteristic. Two or more generations may be grown to ensure that the expression of the desired phenotypic characteristic is stably maintained and inherited and then seeds harvested to ensure that expression of the desired phenotypic characteristic has been achieved. Thus as used herein, "transformed seeds" refers to seeds that contain the nucleotide construct stably integrated into the plant genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. The regenerated plants are generally self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants.

All publications and patent applications are herein incorporated by reference to the same extent as if each individual publication or patent application was specifically and individually indicated to be incorporated by reference.

EXAMPLES

Figure 1:
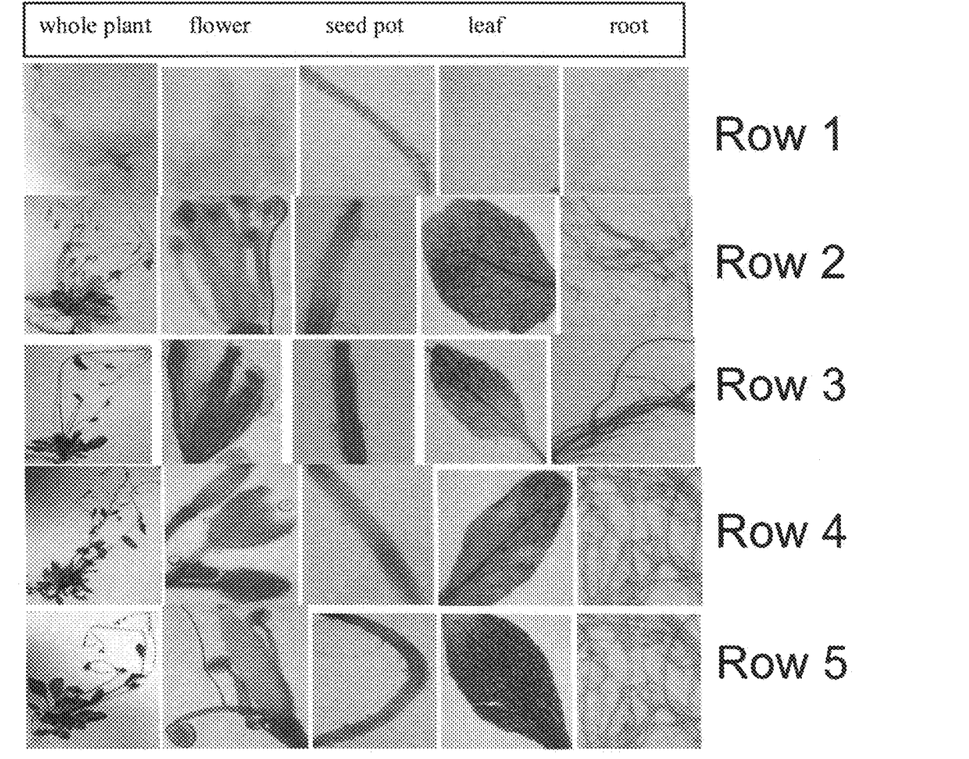
FIG. 1. The transgenic plant that was not induced by stress (first row), showing no gene expression, indicated by no or little blue/bluegreen color. When transgenic plants were induced by high temperature (Row 2), low temperature (Row 3), drought (Row 4), and flooding (Row 5), plants showed very strong expression of GUS gene by deep blue/bluegreen color (the second to fifth row, respectively).

To confirm that the promoter of SEQ ID NO: 1 is inducible by various stresses, the promoter fused with the GUS gene, which makes plant tissue blue/bluegreen upon expression. The gene construct was introduced into *Arabidopsis* and the plants were then exposed to various environmental stresses. The transgenic plants, without stress treatment (the first row in FIG. 1), showed no GUS gene expression (indicated by no/little blue/bluegreen color). When treated with stresses (high and low temperatures, drought, and flooding—second through fifth rows), the GUS gene was highly expressed (within 8 hours of exposure to stress treatment), demonstrating that the promoter of SEQ ID NO: 1 is a broad stress-inducible promoter.

We claim:

1. An isolated nucleic acid molecule comprising SEQ ID NO: 1.

2. A DNA construct comprising SEQ ID NO: 1 operably linked to a heterologous nucleotide sequence of interest.

3. A vector comprising the DNA construct of claim 2.

4. A plant cell having stably incorporated into its genome the DNA construct of claim 2.

5. The plant cell of claim 4, wherein said plant cell is from a monocot.

6. The plant cell of claim 4, wherein said plant cell is from a dicot.

7. A plant having stably incorporated into its genome the DNA construct of claim 2.

8. The plant of claim 7, wherein said plant is a monocot.

9. The plant of claim 7, wherein said plant is a dicot.

10. A transgenic seed of the plant of claim 7, wherein the seed comprises the DNA construct.

11. The plant of claim 8, wherein the heterologous nucleotide sequence of interest encodes a gene product that confers herbicide, salt, heat, cold, flood, drought, pathogen, or insect resistance.

12. A method for expressing a heterologous nucleotide sequence in a plant, said method comprising introducing into a plant a DNA construct according to claim 2 and expressing said heterologous nucleotide sequence.

13. The method of claim 12, wherein said plant is a dicot.

14. The method of claim 12, wherein said plant is a monocot.

15. The method of claim 14, wherein the heterologous nucleotide sequence encodes a gene product that confers herbicide, salt, heat, cold, flood, drought, pathogen, or insect resistance.

16. A method for introducing a heterologous nucleotide sequence into a plant cell comprising introducing into a plant cell a DNA construct according to claim 2.

17. The method of claim 16, wherein said plant cell is from a monocot.

18. The method of claim 16, wherein said plant cell is from a dicot.

19. A method for selectively expressing a heterologous nucleotide sequence in a plant cell comprising introducing into a plant cell a DNA construct according to claim 2, regenerating a transformed plant from said plant cell and exposing said transformed plant to an environmental stress selected from heat, cold, drought or flooding.

* * * * *

UNITED STATES PATENT AND TRADEMARK OFFICE
CERTIFICATE OF CORRECTION

PATENT NO. : 8,471,100 B2
APPLICATION NO. : 12/770943
DATED : June 25, 2013
INVENTOR(S) : Max Zong-Ming Cheng and Xia Ye Page 1 of 1

It is certified that error appears in the above-identified patent and that said Letters Patent is hereby corrected as shown below:

In the Specifications

Column 4,
Line 8, "*J. Viol. Biol.*" should read --*J. Mol. Biol.*--.

Column 12,
Line 53, "*J. Bacteria*" should read --*J. Bacteriol.*--.

Signed and Sealed this
First Day of October, 2013

Teresa Stanek Rea
*Deputy Director of the United States Patent and Trademark Office*